(12) United States Patent
Hildebrand

(10) Patent No.: US 7,931,920 B2
(45) Date of Patent: Apr. 26, 2011

(54) METHOD FOR THE ISOLATION OF NUCLEIC ACIDS FROM ANY STARTING MATERIAL

(75) Inventor: Timo Hildebrand, Hoenow (DE)

(73) Assignee: AJ Innuscreen GmbH, Berlin (DE)

( * ) Notice: Subject to any disclaimer, the term of this patent is extended or adjusted under 35 U.S.C. 154(b) by 6 days.

(21) Appl. No.: 12/128,213

(22) Filed: May 28, 2008

(65) Prior Publication Data

US 2009/0047724 A1   Feb. 19, 2009

Related U.S. Application Data

(63) Continuation of application No. PCT/EP2006/068980, filed on Nov. 28, 2006.

(30) Foreign Application Priority Data

Nov. 28, 2005   (DE) .......................... 10 2005 057 334

(51) Int. Cl.
*A01N 59/00* (2006.01)
*C12Q 1/58* (2006.01)
*C12P 7/06* (2006.01)
*C12N 9/48* (2006.01)

(52) U.S. Cl. ........... 424/600; 435/12; 435/161; 435/212

(58) Field of Classification Search ........................ None
See application file for complete search history.

(56) References Cited

U.S. PATENT DOCUMENTS 6,218,531 B1 * 4/2001 Ekenberg .................. 536/25.41
2005/0164260 A1    7/2005 Chen

FOREIGN PATENT DOCUMENTS

| EP | 0 818 461 | 1/1998 |
|---|---|---|
| WO | WO 95/34569 | 12/1995 |
| WO | WO 2004/055207 | 7/2004 |
| WO | WO 2005/007895 | 1/2005 |
| WO | WO 2006/052680 | 5/2006 |

OTHER PUBLICATIONS

Hourfar et al, Clinical Chemistry (2005) vol. 51, No. 7, pp. 1217-1222.
Ingram, Journal of Bacteriology, (1981) vol. 146, No. 1, pp. 331-336.

* cited by examiner

*Primary Examiner* — Kenneth R. Horlick
*Assistant Examiner* — David C Thomas
(74) *Attorney, Agent, or Firm* — Oblon, Spivak, McClelland, Maier & Neustadt, L.L.P.

(57) ABSTRACT

A composition suitable for the isolation of a nucleic acid from a material containing the nucleic acid contains at least one buffer with a chaotropic component; at least one proteolytic enzyme; at least one buffer with an non-chaotropic component; at least one alcoholic component; and a detergent.

13 Claims, No Drawings

METHOD FOR THE ISOLATION OF NUCLEIC ACIDS FROM ANY STARTING MATERIAL

BACKGROUND OF THE INVENTION

1. Field of the Invention

The invention relates to a universal method for isolating nucleic acids from very different starting materials containing nucleic acids, wherein the method guarantees a very high quality of the isolated nucleic acids as well as allows the isolation of quantitative yields.

2. Discussion of the Background

Under conventional conditions, the isolation of DNA from cells and tissues is carried out such that the starting materials containing the nucleic acids are digested under highly denaturing and reducing conditions with, in part, the use of protein-degrading enzymes, the released nucleic acid fraction is then purified in phenol/chloroform extraction stages and the nucleic acids are isolated by dialysis or ethanol precipitation from the aqueous phase (Sambrook, J., Fritsch, E. F. und Maniatis, T., 1989, CSH, "Molecular Cloning").

These conventional methods for the isolation of nucleic acids from cells and especially from tissues are very time consuming (in part longer than 48 h), require considerable apparative expenditure and moreover are not realizable under field conditions. In addition such methods are hazardous to health owing to the chemicals used in amounts that are not inconsiderable, such as phenol and chloroform.

Different alternative methods for the isolation of nucleic acids from different biological starting materials allow the elaborate and health-damaging phenol/chloroform extraction of nucleic acids to be circumvented and a reduction in time expenditure to be achieved.

All of these methods are based on a method for the preparative and analytical purification of DNA fragments from agarose gels developed and described for the first time by Vogelstein and Gillespie (Proc. Natl. Acad. Sci. USA, 1979, 76, 615-619). The method combines the dissolution in a saturated solution of a chaotropic salt (NaI) of the agarose containing the bands of the DNA to be isolated with binding of the DNA to glass particles. The DNA fixed to the glass particles is then washed with a wash solution (20 mM Tris HCl [pH 7.2]; 200 mM NaCl; 2 mM EDTA; 50% v/v ethanol) and then separated from the support particles.

Until now this method has undergone a series of modifications and is currently used for different methods for the extraction and purification of nucleic acids from different sources (Marko, M. A., Chipperfield, R. und Birnboim, H. G., 1982, Anal. Biochem., 121, 382-387).

In addition, a multiplicity of reagent systems exists worldwide today, predominantly for the purification of DNA fragments from agarose gels and for the isolation of plasmid DNA from bacterial lysates, and also for the isolation of longer chain nucleic acids (genomic DNA, cellular total RNA) from blood, tissues or also cell cultures.

All these commercially available kits are based on the well-known principle of binding nucleic acids to mineral supports in the presence of solutions of different chaotropic salts, and use suspensions of finely-milled glass powder (e.g. Glasmilk, BIO 101, La Jolla, Calif.), diatomaceous earths (Sigma company) or silica gels as support materials.

A method for the isolation of nucleic acids is illustrated which is practicable for a number of different applications proposed in U.S. Pat. No. 5,234,809 (Boom). A method is described therein for the isolation of nucleic acids from starting materials containing nucleic acids, whereby the starting material is incubated with a chaotropic buffer and a DNA-binding solid phase. The chaotropic buffer carries out both the lysis of the starting material as well as the binding of the nucleic acids to the solid phase. The method is well suited for the isolation of nucleic acids from small amounts of sample and finds practical use particularly in the area of the isolation of viral nucleic acids.

Specific modifications of these methods concern the use of novel support materials which have applicative advantages for particular problems (WO-A 95/34569).

More recent patent applications disclose that so-called anti-chaotropic salts can be used very efficiently and successfully as components of lysis/binding buffer systems for the adsorption of nucleic acids to silicate materials known and used by the person skilled in the art (EP 1135479). The advantage of this method is that by circumvention of the use of chaotropic salts a clearly lower hazard to health is posed by the extraction system. However, on the other hand, high salt concentrations (>1.5 M) are required in the lysis buffer for an efficient isolation of nucleic acids from a complex biological sample especially with respect to a highest possible nucleic acid recovery. Thus, the document discloses that the lysis buffers used contain salt concentrations of 1.5 M-3 M.

A method is described in DE 4321904 in which an efficient isolation of nucleic acids is possible with a combination of chaotropic high salt buffer in with alcoholic components. The lysis buffers disclosed in DE 4321904 thereby always contain salt concentrations of 4 M-8 M; guanidine hydrochloride, guanidine thiocyanate or potassium iodide in particular are used as salts. It is known that these salts bring about lysis of the starting material as well as potent inactivation of nucleolytic enzymes. The addition of an alcohol is carried out after lysis of the starting material. The patent discloses that the addition of the alcoholic component to the high salt lysis buffer mediates a highly efficient binding of the nucleic acids to the silicate filter material employed. The disadvantage of the use of lysis buffers with high ion strength chaotropic salts is, however, always the restricted and also inefficient use of additional proteolytic enzymes for an effective digestion of complex biological samples, for these enzymes are themselves damaged by the protein-denaturing action of chaotropic buffers. Furthermore, extensive wash stages are needed subsequently to remove the high salt concentrations from the adsorption material employed. It is known to the person skilled in the art that chaotropic salts exert a high inhibitory action on a number of down-stream applications.

Analysis of the state of the art points out quite impressively that a plurality of possibilities exists for binding nucleic acids to solid support materials, in particular silicon-based mineral support materials, then to wash and to release once more the nucleic acids from the support material. It thereby becomes very clear that so-called chaotropic salts or so-called anti-chaotropic salts are added for the isolation of nucleic acids from complex biological samples.

Chaotropic components are a substances that destroy regular structures of liquid water based on the formation of hydrogen bonds, in that they inhibit the formation of $H_2O$ cage structures necessary for solvation. Examples of chaotropic components are thiocyanates, iodides or perchlorates.

Anti-chaotropic components are substances that enhance regular structures of liquid water based on the formation of hydrogen bonds. Examples of anti-chaotropic components are ammonium, sodium or potassium salts.

Non-chaotropic components are, for example salts, that are between chaotropic and anti-chaotropic salts, and include for example, magnesium chloride or aluminium chloride. Non-chaotropic compounds do not enhance or destroy regular structures of liquid water based on the formation of hydrogen bonds. Non-chaotropic substances are, for example, those in the middle of the Hofmeister series of salts.

The advantages of the use of chaotropic salts for processes for the isolation and purification of nucleic acids are founded in the fact that these salts and buffers derived from them effect an efficient denaturing of proteins. If necessary, this makes possible the isolation of nucleic acids even from complex biological samples, without the use of proteolytic enzymes. A further advantage consists in the fact that chaotropic salts, as components of lysis buffers, also effect a potent inactivation of RNases, in particular in the isolation of RNA. It is, however, disadvantageous that the use of DNA and RNA extraction procedures on the basis of chaotropic salts is always bound to high ion strengths. In low concentrations, an efficient bonding of nucleic acids to chromatographic materials used until now is not possible. This has the result, among others, that washing steps known to those skilled in the art are very complex, founded in separating the high salt concentrations from the final DNA or RNA to be isolated. It is also known that chaotropic components exert a high inhibitory action on a number of down-stream applications. What is more, chaotropic salts are hazardous to health and, in the end, also very cost-intensive.

Advantages of the input of so-called anti-chaotropic salts or non-chaotropic salts (in the patent application cited, this means the groups of the salts which stand at the other end of the Hofmeister Series in relation to the chaotropic salts) consist in the fact that buffer formulations derived from these salts can also be employed for the isolation of nucleic acids. However, as these salts are so-called protein-stabilizing salts, the digestion of complex biological samples always takes place only in the presence of proteolytic enzymes. The efficiency of lysis processes is thereby, as a rule, always worse than with the use of chaotropic salts as a component of lysis buffers. What is more, it is disadvantageous that, particularly in the isolation of RNA from complex biological samples, no inactivation of RNases takes place. This has the result that an efficient isolation of RNA by means of non-chaotropic buffer systems is not possible. It is shown in the analysis of the background art to date that ion strengths of >1M must be introduced for anti-chaotropic methods for the isolation of nucleic acids as well, in order to achieve an efficient and quantitative isolation of nucleic acids.

DETAILED DESCRIPTION OF THE INVENTION

Therefore, it is an object of the invention to provide a lysis/bonding buffer which eliminates the disadvantages named in the background art.

This and other objects are solved, for example, according to the characteristics of the claims.

The formulations according to the invention for the isolation of nucleic acids from materials containing nucleic acids comprise
at least one buffer with at least one chaotropic component,
at least one proteolytic enzyme,
at least one buffer with at least one non-chaotropic component,
at least one alcohol component,
at least one detergent.

According to a preferred embodiment of the invention, the concentration of the buffer with chaotropic components is less than 100 mM and the concentration of the buffer with non-chaotropic components is less than 1M, preferably less than 500 mM.

Alcoholic components within the meaning of the invention are all water-soluble alcohols such as methanol, ethanol, propanol, isopropanol, ethylene glycol, polyethylene glycol or glycerine. The alcoholic component comprises water-soluble alcohols like methanol, ethanol, propanol, isopropanol, ethylene glycol, polyethylene glycol or glycerol, wherein the portion of alcoholic component comes to 20 to 80 wt. %, preferably 45 to 55 wt. %.

At least one of the following substances: polyvinylpyrrolidine, CTAB, Triton X-100, N-lauryl-sarcosine, sodium citrate, DDT or Tween 20 can be introduced as detergent component.

CTAB is cetrimonium bromide (($C_{16}H_{33}$)$N(CH_3)_3Br$). It is a cationic surfactant.

Triton X-100 ($C_{14}H_{22}O(C_2H_4O)n$) is a nonionic surfactant which has a hydrophilic polyethylene oxide group (on average it has 9.5 ethylene oxide units; n=9-10) and a hydrocarbon lipophilic or hydrophobic group. The hydrocarbon group is a 4-(1,1,3,3-tetramethylbutyl)-phenyl group. Other names for Triton X-100 include polyethylene glycol p-(1,1,3,3-tetramethylbutyl)-phenyl ether, octyl phenol ethoxylate, polyoxyethylene octyl phenyl ether, 4-octylphenol polyethoxylate, Mono 30, TX-100, t-octylphenoxypolyethoxyethanol and Octoxynol-9.

DDT is dichloro-diphenyl-trichloroethane, $C_{14}H_9Cl_5$.

Polysorbate 20 (commercially also known as Tween 20) is a polysorbate surfactant ($C_{58}H_{114}O_{26}$). The IUPAC name is polyoxyethylene (20) sorbitan monolaurate.

Any support materials can be used as solid phase—known negative functional surfaces and positively charged nylon membranes, polysulphone membranes, polyethersulphone membranes, PVDF membranes, membranes from acrylic polymers, ion exchange membranes, polyethylene frits or simple filter papers as well as magnetic iron oxide particles, silicate particles.

The method according to the invention for the isolation of nucleic acids from materials containing nucleic acids by use of formulations according to the invention comprises the following steps:
lysis of the starting material,
preliminary filtration if necessary, binding the nucleic acids to a solid phase,
washing of the bound nucleic acids, and
elution of the bound nucleic acids.

One or more nucleic acids, such as DNA and RNA, can be isolated.

According to a preferred embodiment of the method according to the invention, a mixture of a buffer with chaotropic and with non-chaotropic components according to the invention is introduced to wash the bound nucleic acids.

The method according to the invention has the advantage that the same filter material is used for the preliminary filtration and the final adsorption of the nucleic acids.

In one embodiment, after lysis and addition of the solid phase, the nucleic acids are bonded to the solid phase. Afterwards the bonded nucleic acids are washed. This is done, according to conventional techniques, by using special wash buffers. The inventors of the present invention have now surprisingly found that for the washing and the lysis, the same buffer may be used. This results in surprisingly improved purity and yield of the nucleic acid.

The purity of the obtained nucleic acid is >90%, preferably >95%, more preferably >98%, even more preferably >99% and most preferably >99.5%.

The yield of the nucleic acid is >90%, preferably >95%, more preferably >98%, even more preferably >99% and most preferably >99.5%, including >99.6, >99.7, >99.8 and >99.9%.

Likewise an object of the invention is the use of combinations of buffers with chaotropic and with non-chaotropic components for the isolation of nucleic acids from starting materials containing nucleic acids.

According to the invention, a method for the isolation and purification of nucleic acids from complex samples is provided which can be used universally independently of the type of starting material. The method can be carried out in the lysis buffer/binding buffer without the high salt concentrations always necessary to date in conventional methods, which are necessary for a binding of nucleic acids to support materials. What is more, the method makes possible an efficient and fast lysis of the starting material in complex biological samples (e.g. tissues).

It was conventionally assumed that the combination of the chaotropic salts and the non-chaotropic salts or anti-chaotropic salts described in detail as components of buffer formulations for the isolation of nucleic acids from complex biological samples would show no effect.

It emerged surprisingly that the use of lysis buffers for the digestion of a multiplicity of quite different complex biological samples (cells, tissues, plants, bacteria etc.) on the basis of very small concentrations of chaotropic salts in combination with proteolytic enzymes (e.g. proteinase K or lysozme), as well as of a detergent, worked clearly more efficiently and faster in comparison to the lysis buffers used to date, in particular those commercially available as components of nucleic acid cleaning kits. However, it is disadvantageous that the merely small concentrations of chaotropic salts (<100 mM) subsequently allow no efficient connection of the nucleic acids to be isolated to the chromatographic materials known to the person skilled in the art, and particularly that the purity of the nucleic acids to be isolated is also very small. But if one combines the lysis buffer preparation comprising a chaotropic salt, a detergent, a proteolytic enzyme and, if necessary, further components (polyvinylpyrrolidones, EDTA, tris-HCl or others) with a binding buffer which contains a non-chaotropic salt component, an alcohol and a detergent, and subsequently brings this solution into contact with a nucleic acid-binding solid phase (materials based on glass or silica, known in themselves to the person skilled in the art, are used), then an efficient isolation and purification of nucleic acids is possible.

Surprisingly, non-chaotropic salt concentrations necessary for the binding of the nucleic acids are also effective in much smaller concentrations than are introduced in the method known to the person skilled in the art. Therefore salt concentrations of <500 mM are sufficient for an efficient binding of nucleic acids to be isolated. The effect expected to have happened, namely that the action of diametrically functionally opposed salts would cancel each other out, did not come about.

The inventive combination of a lysis buffer with a chaotropic salt component and further additives, with a binding buffer with a non-chaotropic salt component, joins in the most ideal way the advantages of both basic technologies known to the person skilled in the art (chaotropic chemistry and anti-chaotropic chemistry). By means of the lysis buffer described, a highly efficient and fast digestion of the starting material is possible. What is more, the chaotropic component also makes possible the deactivation of nucleic acid-degrading enzymes during the lysis of the starting material. The subsequent addition of a binding buffer which contains a non-chaotropic salt component as well as further additives subsequently facilitates a highly efficient binding of nucleic acids to support materials. The only very small portion of the chaotropic salt component of less than 100 mM, and the only small portion of non-chaotropic salt component of <1 M, thereby means that the salt concentrations to be introduced for the isolation and purification are clearly smaller than known to date to the person skilled in the art. This results in a possible reduction of washing steps (and thereby work-intensive activities) during the nucleic acid extraction, reduces the costs (in particular in the uses for chaotropic salts), is less hazardous to health and also reduces the problem of the carryover of chaotropic salts in downstream applications with the strongly inhibiting effects known. This also affects the purity. A combination of chaotropic and non-chaotropic salts for methods for the isolation and purification and nucleic acids is not known until now.

After the lysis of the starting material and the subsequent mixture with the binding buffer described, the sample is brought into contact with a support material (e.g. a glass fibre thread as a component of a centrifugation filter).

The nucleic acid bound to the filter material can be washed with wash buffers known in themselves, subsequently briefly dried and released once more from the glass fibre material after the addition of water or 10 mM Tris HCl. Surprisingly, it is emerged that the use of a wash buffer which is composed of mixtures of the lysis buffer-binding buffer according to the invention, both the final yield of nucleic acid and the purity of the isolated nucleic acid can be further improved.

Since the lysis buffers used in the method according to the invention contain no components that allow efficient adsorption of nucleic acids, it is also possible to carry out, for example, necessary preliminary filtration processes through the same filter material that is also finally used for the adsorption of the nucleic acids. This represents a considerable technological simplification. Thus, for example after lysis of a plant sample, the lysate can be centrifuged through a glass fibre filter matrix as part of a centrifugation column to remove unlysed plant materials and inhibitory components. The filtrate is then treated with a binding buffer and transferred to a further centrifuge column with glass fibre matrix. The nucleic acids bind to the fibres of the glass fibre matrix, are washed with an alcohol-containing wash buffer and the bound nucleic acids are then finally eluted from the glass fibre matrix by the addition of, for example, water.

This is equally valid for complex biological samples such as faecal samples or also, i.a., whole blood. Such a simplification cannot be carried out with the previously known systems and methods, which also contain the salt components necessary for the adsorption of the nucleic acids in the lysis buffer.

The method according to the invention surprisingly shows a further quite significant new effect.

It is known that the support materials employed for the isolation and purification (in combination with the known high salt buffers and optionally alcohols) are glass, ceramic, quartz, silica gels, aerosils, diatomaceous earths, etc. These materials can be porous or non-porous. They can be components of e.g. centrifugation units (centrifugation filter columns) etc. as suspension or also as threads, gels, wool or matting. It is also known to the person skilled in the art that binding can take place of polyanions like e.g. DNA to negative functional surfaces. This basic knowledge represents the scientific background for the use of negative or potentially negative solid phases for the binding of nucleic acids with the known high salt buffers.

Surprisingly, the combination, described in the method according to the invention, of a lysis buffer with a chaotropic salt component and a binding buffer with a non-chaotropic salt component shows that an efficient connection of nucleic acids is also possible to a multiplicity of support materials not as yet introduced for the isolation and purification of nucleic acids. In addition to the possibility of the use of support materials known in themselves (in particular with negative functional charges), physically/chemically quite different support material could be used for the isolation and purification of nucleic acids. Named here as examples are positively charged nylon membranes, polysulphone membranes, polyethersulphone membranes, PVDF membranes, membranes from acrylic polymers, ion exchange membranes, polyethylene frits and even simple filter papers (e.g. paper filters). This is also all the more surprising since a number of the membranes described have chemically inert, neutral surfaces and are actually used in practice for filtrations with the objective of having no binding affinities for biomolecules.

Moreover, particles are also suitable for the binding of nucleic acids with the described methods (e.g. functionalised magnetic iron oxide particles, silica particles, etc.).

The binding and the final desorption of the nucleic acids to and from these quite different support materials can take place under the same lysis/binding buffer conditions.

This observation suggests a totally novel mechanism through which the process of isolation and purification of nucleic acids is realized.

It becomes clear, however, that the practicability of using different support materials will facilitate quite new product developments in the sector of isolation and purification of nucleic acids. The appropriate combination of lysis/binding buffer with specific support materials offers henceforth the possibility of totally new solution approaches for the isolation of nucleic acids. This is all the more interesting, since methods of molecular sample preparation within the context of rapidly developing molecular diagnostics are in principle becoming increasingly more essential in all aspects of our life.

Having generally described this invention, a further understanding can be obtained by reference to certain specific examples which are provided herein for purposes of illustration only, and are not intended to be limiting unless otherwise specified.

EXAMPLES

In the following the invention is defined more closely by means of an exemplary embodiment. The example does not thereby represent any limitation of the invention. The exemplary embodiments 2-4 serve as proof that the inventive positive effect of the combination of chaotropic and non-chaotropic buffers is not limited to the combination of 90 mM urea in the lysis buffer and 250 mM magnesium chloride in the binding buffer.

EXEMPLARY EMBODIMENTS

Example 1

Comparison of the isolation of genomic DNA from tissue samples using lysis buffer/binding buffers on the basis of only chaotropic salts, only non-chaotropic salts and the method according to the invention.

In each case, 10 mg tissue material (pig's liver) were incubated for 30 min in 400 μl lysis buffer A (4M guanidinium thiocyanate, 1% N-lauroyl sarcosine, 2 mM EDTA), lysis buffer B (1.5 M ammonium chloride, 2% CTAB, 10 mM tris-HCl, 2% PVP) as well as lysis buffer C (0.5% SDS, 10 mM tris HCl, 2 mM EDTA, 90 mM urea) in a 1.5 ml reaction vessel, to which 25 μl proteinase K (20 mg/ml) were added, as well as RNase A at 50° C. while being continually shaken. After lysis of the starting material the lysis assay was centrifuged at full speed for 1 min to remove unlysed components. The excess was treated as follows:

1. Lysis assay with lysis buffer A directly on a spin filter column with glass fibre material,
2. Addition of 200 μl of a binding buffer (Triton X-100/isopropanol) to the lysis assay with lysis buffer B, afterwards assay directly on a spin filter column with glass fibre material,
3. Addition of 400 μl of a binding buffer (250 mM $MgCl_2$, Tween/isopropanol) to the lysis assay with lysis buffer C, subsequent addition directly onto a spin filter column with glass fibre material.

Subsequent centrifugation of the solutions over the glass fibre filter.

The filtrate was subsequently discarded and the filter materials with the variants of the lysis buffer A and lysis buffer B as well as the variants with lysis buffer C were washed twice with 750 μl of a wash buffer (50 mM NaCl; 10 mM tris HCl; 1 mM EDTA; 70% v/v ethanol) each. In a further extraction variant with the method according to the invention (lysis buffer C), the filters are washed once with 500 μl from a mixture of the lysis buffer C introduced, as well as the binding buffer appertaining to it, and subsequently washed again with the standard wash buffer.

After the removal of the ethanol in a brief centrifugation step (12,000 rpm for 2 min) the nucleic acids were eluted by the addition of 200 μl of an elution buffer (10 mM Tris-HCl; pH 8.5) by centrifugation for 1 min at 10,000 rpm. Next spectrophotometric measurement of the DNA was carried out.

The results are shown in the following table. In each case 3 extractions were carried out and the measurement values calculated and averaged after spectrophotometric measurement.

| Lysis buffer/binding buffer | Yield | Ratio $A_{260}:A_{280}$ |
| --- | --- | --- |
| Chaotropic (variant lysis buffer A) | 8.2 μg | 1.4 |
| Non-chaotropic (variant lysis buffer B) | 21.2 μg | 1.5 |
| Combination of chaotropic/non-chaotropic (variant lysis buffer C) | 28.4 μg | 1.7 |
| Combination of chaotropic/non-chaotropic (variant lysis buffer C) with wash buffer from a mixture of the lysis buffer/binding buffer introduced | 36.2 μg | 1.8 |

The lysis buffers A and B are known from patent applications and are exemplary for both basic technologies (chaotropic chemistry and non-chaotropic chemistry).

The superiority of the extraction according to the invention is clearly seen. After 30 min. of lysis time, the tissue samples which were treated by the method according to the invention were completely lysed, the other samples only partially so, however.

The results show that the isolation of nucleic acids using the method according to the invention is very efficient due to the combination of chaotropic salts and non-chaotropic salts (in the lysis buffer and binding buffer), the lysis of the starting material is carried clearly faster and both, a high purity and high yield, can be achieved. If, instead of the alcoholic standard wash buffer introduced until now, a mixture of the lysis/binding buffer according to the invention with something for washing is introduced, then this combination leads again to an improvement of the extraction.

Example 2

Combination of a lysis buffer with binding buffers, which contain further different non-chaotropic salts alongside magnesium chloride. Use of the buffer corresponding to the method according to the invention for the isolation of genomic DNA from a complex biological sample (tissue)
Lysis Buffer and Binding Buffer Introduced:
Lysis buffer: 90 mM urea/0.5% SDS
Binding buffer H1: 250 mM magnesium chloride; 50% isopropanol; 40% Tween 20;
Binding buffer H2:
Binding buffer H3: 250 mM calcium chloride; 50% isopropanol; 40% Tween 20;
Binding buffer H4: 250 mM ammonium chloride; 50% isopropanol; 40% Tween 20.
Extraction Protocol
1. Approx. 40 mg liver tissue (mouse) was treated per batch with 400 µl lysis buffer and 25 µl proteinase K and lysed at 50° C.
2. After lysis there took place the addition of 400 µl binding buffer (H1; H2; H3; H4). Lysis assay and binding buffer were mixed thoroughly with a pipette.
3. Transfer of the sample to a centrifuge column with glass fibre filter material and centrifugation at 10,000×g for 1 min. Rejection of the filtrate.
4. Subsequently wash twice with ethanolic wash buffer (70% ethanol, sodium chloride; Tris HCl).
5. Drying of the column by centrifugation for 2 min at 10,000×g.
6. Elution of the DNA by addition of 200 µl of an elution buffers (10 mM Tris HCl); Centrifugation at 5,000×g for 1 min.

Next the isolated DNA was measured spectrophotometrically. The measurement values obtained are average values each from 3 preparations per binding buffer used.
Result

| Lysis buffer/<br>binding buffer combination | Ratio<br>A260:A280 | Total yield of DNA |
|---|---|---|
| Lysis buffer: 90 mM urea/0.5% SDS<br>Binding buffer: H1 | 2.0 | 68 µg |
| Lysis buffer: 90 mM urea/0.5% SDS<br>Binding buffer: H2 | 1.95 | 69 µg |
| Lysis buffer: 90 mM urea/0.5% SDS<br>Binding buffer: H3 | 1.95 | 65 µg |
| Lysis buffer: 90 mM urea/0.5% SDS<br>Binding buffer: | 1.96 | 64 µg |

Conclusion:

The combination of the present lysis buffer with different binding buffers (differentiation of the binding buffer into the non-chaotropic salts introduced) leads to the result that the non-chaotropic salts used are all excellently suited for the isolation of nucleic acids. For this reason, this result also shows that it is not only magnesium chloride that brings about the positive effect according to the invention of the combination of a lysis buffer with a chaotropic salt and a binding buffer with a non-chaotropic salt, but other non-chaotropic salts (e.g. lithium chloride; calcium chloride; ammonium chloride) likewise support the effect according to the invention and can be used as non-chaotropic salts in binding buffers.

Example 3

Use of lysis buffers which differ as to chaotropic salts introduced, and combination of these Lysis buffers with two different binding buffers in order to prove that the invention does not only deal with the use of urea as chaotropic salt in the lysis buffer. Both chaotropic salts, urea and sodium perchlorate, were introduced. Lysis buffer and binding buffer introduced:
Lysis buffer A: 90 mM urea/0.5% SDS;
Lysis buffer B: 90 mM sodium perchlorate/0.5%;
Binding buffer H1: 250 mM magnesium chloride; 50% isopropanol; 40% Tween 20;
Binding buffer H3: 250 mM calcium chloride; 50% isopropanol; 40% Tween 20.
Extraction Protocol
1. Approx. 25 mg liver tissue (mouse) per batch was treated with 400 µl lysis buffer (lysis buffer A; lysis buffer B) and 25 µl proteinase K, and lysed at 50° C.
2. After lysis the addition of 400 µl binding buffer (H1; H3) took place. Lysis assay and binding buffer were mixed thoroughly with a pipette.
3. Transfer of the sample to a centrifuge column with glass fibre filter material and centrifugation at 10,000×g for 1 min. Rejection of the filtrate. Subsequently wash twice with ethanolic wash buffer (70% ethanol, sodium chloride; Tris HCl).
4. Drying of the column by centrifugation for 2 min at 10,000×g. Elution of the DNA by addition of 200 µl of an elution buffer (10 mM Tris HCl); centrifugation at 5,000×g for 1 min.

Next the isolated DNA was measured spectrophotometrically. The measurement values obtained are average values each from 3 preparations per binding buffer used.
Result

| Lysis buffer/<br>binding buffer combination | Ratio<br>A260:A280 | Total yield of DNA |
|---|---|---|
| Lysis buffer: 90 mM urea/0.5% SDS<br>Binding buffer: H1 | 1.96 | 41 µg |
| Lysis buffer: 90 mM urea/0.5% SDS<br>Binding buffer: H3 | 1.98 | 39 µg |
| Lysis buffer: 90 mM<br>Sodium perchlorate/0.5% SDS<br>Binding buffer: H1 | 1.94 | 37 µg |
| Lysis buffer: 90 mM<br>Sodium perchlorate/0.5% SDS<br>Binding buffer H3 | 1.98 | 41 µg |

Conclusion:

The combination of the present lysis buffer with different binding buffers (differentiation of the binding buffer into the non-chaotropic salts introduced) leads to the result that the non-chaotropic salts used are all excellently suited for the isolation of nucleic acids. For this reason, this result also shows that it is not only magnesium chloride that brings about the positive effect according to the invention of the combination of a lysis buffer with a chaotropic salt and a binding buffer with a non-chaotropic salt, but other non-chaotropic salts (e.g. lithium chloride; calcium chloride; ammonium chloride) likewise support the effect according to the invention and can be used as non-chaotropic salts in binding buffers.

Example 4

Combination of a lysis buffer with chaotropic salt contained in it and binding buffers which contain non-chaotropic salts, wherein the ion strength of the non-chaotropic salts coming into use in the binding buffer was clearly reduced. The test should emphasise that the combination, depicted in the method, of chaotropic and non-chaotropic salts in lysis buffers and binding buffers allows for the isolation of nucleic acids even with extremely small salt combinations.

Lysis Buffer and Binding Buffer Introduced:
Lysis buffer: 90 mM urea/0.5% SDS;
Binding buffers H5: 100 mM magnesium chloride; 50% isopropanol; 40% Tween 20;
Binding buffer H6: 100 mM lithium chloride; 50% isopropanol; 40% Tween 20;
Binding buffer H7: 100 mM calcium chloride; 50% isopropanol; 40% Tween 20.

Extraction Protocol
1. Approx. 25 mg liver tissue (mouse) was treated per batch with 400 µl lysis buffer and 25 µl proteinase K and lysed at 50° C.
2. After lysis there took place the addition of 400 µl binding buffer each (H5; H6; H7). Lysis assay and binding buffer were mixed thoroughly with a pipette.
3. Transfer of the sample to a centrifuge column with glass fibre filter material and centrifugation at 10,000×g for 1 min. Rejection of the filtrate.
4. Subsequently wash only once with ethanolic wash buffer (70% ethanol, sodium chloride; Tris HCl).
5. Drying of the column by centrifugation for 2 min at 10,000×g.
6. Elution of the DNA by addition of 200 µl of an elution buffers (10 mM Tris HCl); Centrifugation at 5,000×g for 1 min.

Next the isolated DNA was measured spectrophotometrically. The measurement values obtained are average values each from 3 preparations per binding buffer used.

Result

| Lysis buffer/binding buffer combination | | Total yield of DNA |
|---|---|---|
| Lysis buffer: 90 mM urea/0.5% SDS Binding buffer: H5 | 1.73 | 43 µg |
| Lysis buffer: 90 mM urea/0.5% SDS Binding buffer: | 1.80 | 42 µg |
| Lysis buffer: 90 mM urea/0.5% SDS Binding buffer: H7 | 1.71 | 44 µg |

Conclusion:
The combination of the present lysis buffer with different binding buffers (differentiation of the binding buffer into the non-chaotropic salts introduced) leads to the result that the non-chaotropic salts used are all excellently suited for the isolation of nucleic acids. With it, this result also shows that it is not only magnesium chloride which brings about the positive effects according to the invention of the combination of a lysis buffer with a chaotropic salt and a binding buffer with a non-chaotropic salt, but other non-chaotropic salts can be used as well. What is more, the result makes formidably clear that, according to the inventive method, very many fewer ion strengths are necessary for the isolation of nucleic acids by the principle, known to those skilled in the art, of binding nucleic acids to solid mineral materials than is known to date according to the background art. In this way, the combination of the lysis buffer/binding buffer according to the invention makes possible an extremely efficient isolation of nucleic acids without the high salt concentrations in the buffer systems introduced which had been necessary until now. This also makes it possible, as in the test described, to reduce the necessary wash steps.

German patent application 10 2005 057 334.7 filed Nov. 28, 2005, and international application PCT/EP2006/068980, filed Nov. 28, 2006, are incorporated herein by reference.

Numerous modifications and variations on the present invention are possible in light of the above teachings. It is therefore to be understood that within the scope of the appended claims, the invention may be practiced otherwise than as specifically described herein.

What is claimed is:
1. A composition, comprising:
at least one chaotropic component;
at least one proteolytic enzyme;
at least one non-chaotropic component;
at least one alcoholic component; and
a detergent;
wherein
said composition is suitable for the isolation of a nucleic acid from a material containing said nucleic acid; and
a concentration of the at least one chaotropic component in the composition is lower than 100 mM.
2. The composition according to claim 1, wherein a concentration of the at least one non-chaotropic component in the composition is lower than 1M.
3. The composition according to claim 1, wherein a concentration of the at least one non-chaotropic component in the composition is lower than 500 mM.
4. The composition according to claim 1, wherein said alcoholic component is selected from the group consisting of water-soluble alcohols and mixtures thereof.
5. The composition according to claim 1, wherein an amount of said alcoholic component in the composition is from 20 to 80 wt. %.
6. The composition according to claim 1, wherein said detergent is selected from the group consisting of polyvinylpyrrolidine, cetrimonium bromide, polyethylene glycol p-(1,1,3,3-tetramethylbutyl)-phenyl ether, N-lauryl-sarcosine, sodium citrate, dichloro-diphenyl-trichloroethane, polyoxyethylene (20) sorbitan monolaurate and mixtures thereof.
7. The composition according to claim 1, further comprising a solid phase.
8. The composition according to claim 1, further comprising a support material as a solid phase.
9. The composition according to claim 1, further comprising a solid phase selected from the group consisting of negative functional surfaces, positively charged nylon membranes, polysulphone membranes, polyethersulphone membranes, PVDF membranes, membranes comprising acrylic polymers, ion exchange membranes, polyethylene frits, filter papers, magnetic iron oxide particles, silicate particles and combinations thereof.
10. The composition according to claim 1, wherein said alcoholic component is a water-soluble alcohol selected from the group consisting methanol, ethanol, propanol, isopropanol, ethylene glycol, polyethylene glycol, glycerine and mixtures thereof.

11. The composition according to claim 1, wherein an amount of said alcoholic component in the composition is from 45 to 55 wt. %.

12. The composition according to claim 1, wherein a concentration of the at least one non-chaotropic component in the composition is 250 mM or less.

13. The composition according to claim 1, further comprising a solid phase selected from the group consisting of negative functional surfaces, positively charged nylon membranes, polysulphone membranes, polyethersulphone membranes, PVDF membranes, membranes comprising acrylic polymers, ion exchange membranes, polyethylene frits, filter papers, magnetic iron oxide particles and combinations thereof.

\* \* \* \* \*